United States Patent [19]
Duroselle et al.

[11] Patent Number: 5,951,948
[45] Date of Patent: *Sep. 14, 1999

[54] APPARATUS AND METHOD FOR THE PROCESSING, PARTICULARLY THE DECONTAMINATION, OF MATERIALS

[75] Inventors: Patrick Duroselle, Saint-Herblain, France; Fabrice Laberge, Fribourg, Switzerland

[73] Assignee: Carba Societe Anonyme, Liebefeld, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/702,236

[22] Filed: Aug. 27, 1996

[30] Foreign Application Priority Data

Sep. 8, 1995 [EP] European Pat. Off. ............ 95 810 558

[51] Int. Cl.⁶ ...................................... A61L 2/20
[52] U.S. Cl. ........................... 422/33; 422/292; 422/305
[58] Field of Search .................... 422/28, 30, 32, 422/33, 186.07, 186.16, 224, 305, 906, 292

[56] References Cited

U.S. PATENT DOCUMENTS

| | | | |
|---|---|---|---|
| 2,660,559 | 11/1953 | Prime | 210/67 |
| 3,448,045 | 6/1969 | Hess et al. | 210/63 |
| 4,156,652 | 5/1979 | Wiest | 250/527 |
| 4,309,388 | 1/1982 | Tenney et al. | 422/304 |
| 4,409,183 | 10/1983 | Fischer | 422/68 |
| 4,990,166 | 2/1991 | Babich | 55/228 |
| 5,004,587 | 4/1991 | Tacchi | 422/186.19 |
| 5,069,880 | 12/1991 | Karlson | 422/186.19 |
| 5,082,558 | 1/1992 | Burris | 210/167 |
| 5,087,419 | 2/1992 | Lutz | 422/28 |
| 5,120,512 | 6/1992 | Masuda | 422/297 |
| 5,145,585 | 9/1992 | Coke | 210/695 |
| 5,152,812 | 10/1992 | Kovach | 55/23 |
| 5,190,648 | 3/1993 | Ramsauer | 210/172 |
| 5,527,508 | 6/1996 | Childers et al. | 422/33 |

FOREIGN PATENT DOCUMENTS

| | | |
|---|---|---|
| 0372293-A2 | 6/1990 | European Pat. Off. ........ F24D 17/00 |
| 0442254-A1 | 8/1991 | European Pat. Off. .......... C02I 1/78 |
| 0761237 | 12/1997 | European Pat. Off. .......... A61L 2/20 |
| 1137268 | 1/1957 | France . |
| 2695828-A1 | 3/1994 | France ........................... A61L 11/00 |
| 2059859 | 7/1971 | Germany ........................ C02C 5/04 |
| 3813793 C1 | 4/1989 | Germany ........................ A61L 2/20 |
| 5-115540 | 5/1993 | Japan ............................ A61L 11/00 |
| 6-327748 | 11/1994 | Japan ............................ A61L 2/20 |
| 7-136236 | 5/1995 | Japan ............................ A61L 2/20 |
| 8605100 | 9/1986 | WIPO . |
| 9406483 | 3/1994 | WIPO . |

*Primary Examiner*—Elizabeth McKane
*Attorney, Agent, or Firm*—Limbach & Limbach L.L.P.; Kyla L. Harriel

[57] ABSTRACT

Apparatus for the decontamination, disinfection, or sterilization of materials such as medical waste by exposure to ozonized air comprises a generator of ozonized air, an enclosure for the accumulation of ozonized air, a processing enclosure in which the materials to be processed are placed, and a destroyer of residual ozone leaving the processing enclosure. The ozonized air reaches the processing enclosure via the accumulation enclosure. A vacuum pump operating in air is situated downstream from the ozone destroyer for creating a partial vacuum in the processing enclosure. The generator of ozonized air is connected in open circuit with the accumulation enclosure. The apparatus further comprises an injection valve interposed between the accumulation enclosure and the processing enclosure. The injection valve is controlled in such a way as to periodically to trigger the sudden and forceful injection of ozonized air into the processing enclosure as soon as the pressure drops below a certain limit.

22 Claims, 2 Drawing Sheets

APPARATUS AND METHOD FOR THE PROCESSING, PARTICULARLY THE DECONTAMINATION, OF MATERIALS

This invention relates to apparatus for the processing of materials and to a method of processing materials. More specifically, the invention has to do with the problem of the decontamination, disinfection, and sterilization of materials, e.g., medical waste or materials used in the chemical, pharmaceutical, or farm-produce industries.

European Patent Application No. 95810558.7, filed in the European Patent Office on Sep. 8, 1995 by the present assignee, is included in the present application by reference.

The practitioners of the medical and paramedical professions produce all sorts of refuse of various physical types, such as plastics, textiles, metals, glass, liquids, etc., liable to be contaminated by microbial or viral germs. Such refuse may, for instance, be needles, plastic tubing, compresses, blood bags, various organic tissues, etc., which cannot be eliminated like ordinary waste because of the risk of contamination. Other professions also constantly generate increasing quantities of material which must be decontaminated, sterilized, or disinfected. This is true, for example, of the chemical or farm-produce industries, or of waste-processing or water-purification plants.

The quantity and variety of waste produced is constantly increasing, especially in the medical field. Various methods and apparatus for processing this type of waste have consequently been developed to cope with this demand. For example, waste incinerators utilizing heat to eliminate microbial germs have been proposed. However, such apparatus is not suitable for local processing of waste, e.g., processing on the premises of the practitioner. Other proposals utilize immersion in a disinfectant solution or processing by means of an ionizing solution or ultrasound. All such apparatus, though operating in a generally satisfactory manner, are costly and cumbersome and, consequently, mainly reserved for large-scale operations.

Apparatus for decontamination by means of ozone or an ozone-enriched gas has also been proposed. Such apparatus is particularly suitable for the decontamination or sterilization of medical waste close to the place of production.

International Patent Application Publication No. WO86/05100 describes apparatus for sterilizing medical material by means of gaseous ozone. The waste is placed in a processing enclosure under vacuum. An ozone generator injects ozone into the enclosure, and means are provided for destroying the residual ozone. The ozone generator operates starting from a source of pure oxygen, which involves certain risks associated with the installation, especially the risk of explosion if fat-containing waste comes into direct contact with the oxygen. Moreover, the ozone generator operates from a flow of gas having a high rate of humidity, which impairs its efficiency.

The apparatus described in U.S. Pat. No. 5,120,512 presents similar drawbacks, the ozone always being produced starting from pure oxygen and injected directly into the processing enclosure.

The apparatus disclosed in French Published Patent Application No. 1,137,268 represents an improvement as regards safety, for the ozone is produced starting from air rather than pure oxygen. However, this apparatus does not yield the high concentrations of ozone necessary for thorough decontamination or sterilization of the waste.

Other decontamination apparatus utilizing ozone or ozonized air are described in U.S. Pat. Nos. 4,156,652 and 5,087,419, for example. Such apparatus generally uses a closed circuit established between an ozone generator and a processing enclosure in which the waste to be processed is disposed. Some apparatus further provides means for injecting water or for stirring the gaseous environment or the waste, all with the object of facilitating the action of the ozone and improving its penetration. These measures as a whole cause the generators to operate under poor conditions since the flow of gas passing through them is humid and/or polluted by the processing enclosure and its contents.

Finally, Australian Patent No. 4,823,393 describes a decontamination apparatus using an enclosure for accumulating ozonized air, connected in closed circuit with the ozone generator. This circuit yields high concentrations of ozone in the air within the accumulation enclosure. Moreover, the ozone generators can work under favorable conditions since clean, dry air passes through them. This air having a high concentration of ozone is regularly extracted by a transfer pump and injected into a processing enclosure, independent of the accumulation enclosure, in which the waste to be decontaminated is placed. The transfer pump provided between the accumulation enclosure and the processing enclosure must consequently operate in air very rich in ozone, which necessarily presents numerous problems. Hence the pump must be of costly construction in order to resist the aggressiveness of that gas. Furthermore, the ozonized-air pressure, which is constant throughout the apparatus and during the whole process, does not bring about penetration in depth of the ozonized air into the mass of waste to be processed. What is more, the apparatus continues to operate even if the processing enclosure is not completely fluid-tight, thus posing a safety problem.

Experimentation has shown that the spontaneous decomposition of ozone, whether catalytic or through combination with the waste to be processed, is extremely rapid (barely a few seconds). The quantity of ozone available in the processing enclosure therefore quickly decreases. To compensate for this decrease, large quantities of ozone must be continuously injected into the processing enclosure.

It is an object of this invention to provide a processing apparatus and method which do not have the mentioned drawbacks of prior art apparatus.

A particular object of this invention is to provide processing apparatus in which the ozone-generating means can work with clean, dry air and which needs no pump operating in ozone-rich air.

Another object of the invention is to improve the effectiveness and/or the rapidity of processing by improving the penetration of ozonized air into the waste.

Still another object is to improve the effectiveness and/or the rapidity of processing by using high concentrations of ozone.

A further object is to improve the safety afforded by the apparatus.

To this end, the materials processing apparatus according to the present invention comprises a generator of processing gas, an enclosure for accumulating the processing gas, a processing enclosure into which the materials to be processed can be inserted, a pump capable of creating partial vacuum in the processing enclosure, and a plurality of pipes interconnecting the generator, the accumulation enclosure, and the processing enclosure, the pipes being disposed in such a way that the processing gas coming from the generator can arrive in the processing enclosure after having passed through the accumulation enclosure, the materials being processed by exposure to the processing gas.

The materials processing method of the present invention comprises a plurality of separate steps of injection of a processing gas into a processing enclosure.

In particular, it is intended to achieve these objects through means for creating a partial vacuum in the processing enclosure. This negative pressure makes it possible to improve the penetration of the ozonized air into the waste to be processed, and also to obtain a sudden and forceful injection of ozonized air into the processing enclosure without requiring an injection pump between the accumulation enclosure and the processing enclosure.

In one embodiment of the invention, the pump is not a transfer pump working in ozonized air between the accumulation and processing enclosures but rather a vacuum pump situated downstream from the ozone-destroying device and creating a negative pressure in the processing enclosure. This pump thus operates only in air.

In another embodiment, the ozone-generating means are connected in open circuit with the enclosure for accumulating ozonized air. By means of this arrangement, the pressure in the accumulation enclosure increases along with the ozone concentration.

In a further embodiment, the apparatus comprises an injection valve interposed between the enclosure for accumulating ozonized air and the processing enclosure. This valve is controlled so as to trigger a sudden and forceful injection of ozonized air into the processing enclosure as soon as the pressure within the processing enclosure drops below a certain threshold. Thus, by means of this valve, alternating cycles of forceful injection of ozonized air and of partial vacuum are created in the processing enclosure, which contributes toward improving the efficiency of the apparatus for a given hourly production of the ozone generators.

In still another embodiment, the ozonized air is injected suddenly and forcefully into the processing enclosure owing to the pressure gradient between the accumulation enclosure and the processing enclosure when the injection valve is opened. This pressure gradient permits a forceful, eddying injection of ozonized air, thus improving the penetration of the gaseous mixture.

The alternation of brief phases of injection of air having a high ozone concentration, then of partial vacuum within the processing enclosure, is more effective than continuous injection owing to the spontaneous decomposition of the ozone. For in this way, the concentration of ozone in the processing enclosure remains higher than the biological activity threshold during the entire processing operation.

The injection of ozone is allowed only if the partial vacuum within the processing enclosure reaches a certain value within a certain time. This represents a major safety factor since the injection cannot take place unless the processing apparatus is completely fluid-tight.

In addition, working within the processing enclosure under partial vacuum or at atmospheric pressure minimizes the risk of significant leakage.

Other objects and advantages of the invention will become apparent from the following detailed description of a preferred embodiment thereof, taken in conjunction with the accompanying drawings, in which.

Figure 1:
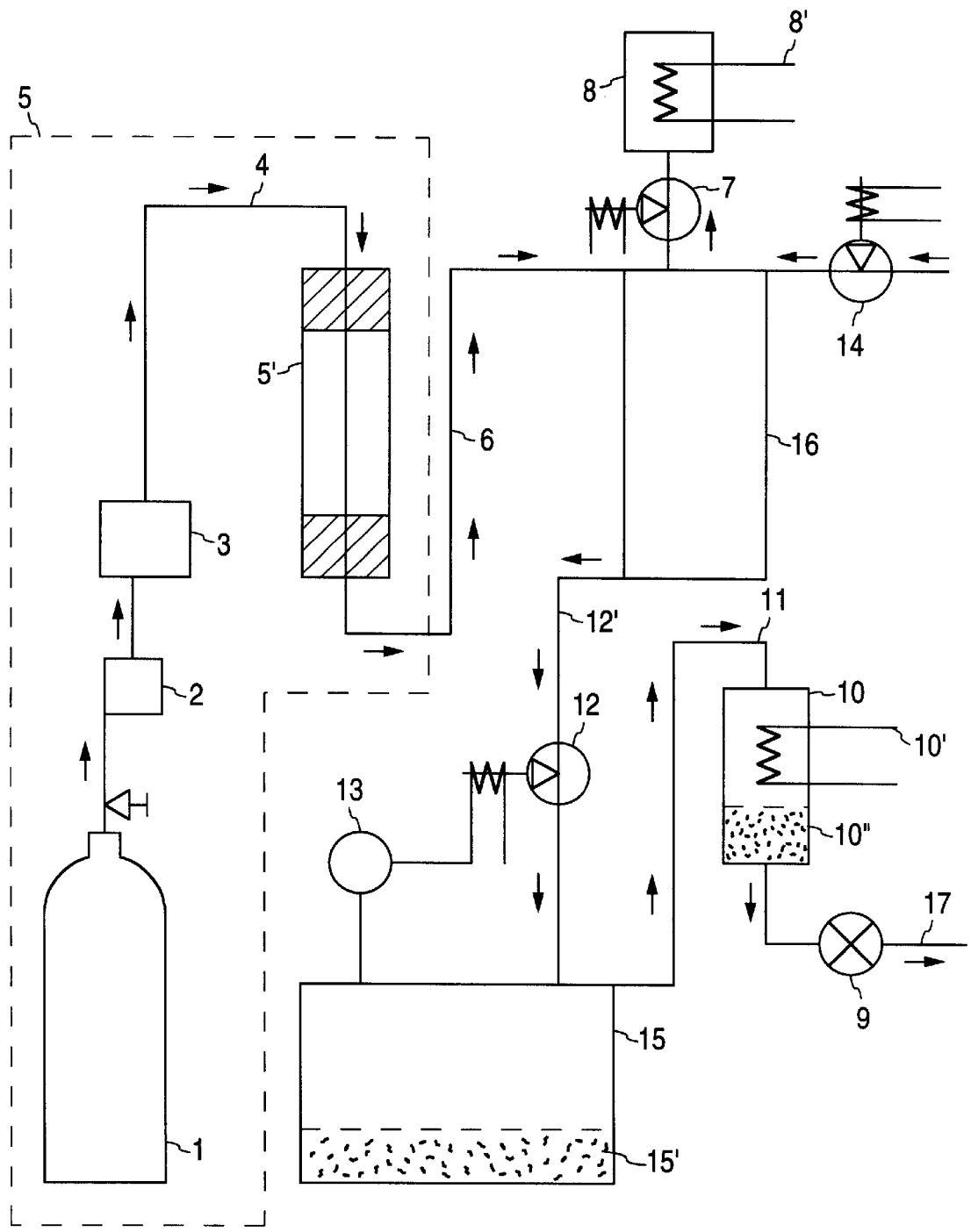
FIG. 1 is an overall diagram of the processing apparatus.

In the embodiment of the invention illustrated in FIG. 1, the decontamination apparatus essentially includes ozone-generating means 5, an enclosure 16 for accumulating ozonized air, a processing enclosure 15 for the waste 15' to be processed, and main ozone-destroying means 10. These various elements are interconnected by an assembly of tubing and valves enabling the decontamination method to be carried out.

Ozone-generating means 5 preferably comprise a source 1 of compressed air, an escape valve 2 functioning as a flowmeter, a drying device 3, a pipe 4, and an ozone generator 5'. All these elements are known per se; in one modification, ambient air may be used instead of a source of compressed air and an escape-valve. The clean air coming from source 1 reaches flowmeter escape-valve 2, is desiccated in drying device 3, and is conveyed through pipe 4 to ozone generator 5'. This generator is of a type known per se, e.g., of the cylinder-wire type described in the previously mentioned Australian Patent No. 4,823,393. As it operates with clean, dry air, its efficiency is very high.

The ozone-enriched air leaves ozone generator 5' though a duct 6 and enters the upper part of accumulation enclosure 16. The means 5 for generating ozonized air are connected in an open loop with enclosure 16. In this enclosure, the pressure therefore increases at the same time as the ozone concentration.

Beyond a predetermined pressure, a safety valve 7 opens in order to exhaust the excess ozonized air to an auxiliary ozone destroyer 8 of a type known per se, comprising an electric heating resistor 8'. Consequently, accidental or momentary overpressure in the accumulation enclosure does not cause ozone to be released into the atmosphere.

A pipe 12' closed by an electrically operated valve 12 connects the bottom of accumulation enclosure 16 to the fluid-tight processing enclosure 15, made of stainless steel or any other suitable material, in which the products 15' to be processed are disposed. Enclosure 15 is closed by a fluid-tight door or cover allowing the waste to be put in. A vacuum pump 9 creates a partial vacuum in main ozone destroyer 10. The latter, of a type known per se, preferably comprises an electric heating resistor 10' and a catalytic decomposer 10" forming an antibacterial filter. The air rid of residual ozone by destroyer 10 is exhausted into the atmosphere through an open-circuit drainpipe 17.

The partial vacuum in main ozone destroyer 10 spreads through a pipe 11 to processing enclosure 15 and to the materials 15' to be processed. At a selected pressure, measured by a vacuostat 13, the electrically operated valve 12 controlled thereby abruptly opens. In a modification, valve 12 opens as soon as the difference in pressure between the accumulation enclosure and the processing enclosure exceeds a certain limit. The overpressurized ozonized air contained in accumulation enclosure 16 then enters processing enclosure 15 suddenly and forcefully. The injection is of the eddying type, thus improving the penetration of the ozonized air into the waste 15'. A time-lag device (not shown) opens an electrically operated valve 14 one or two seconds after the opening of valve 12, thus allowing enclosure 16 for accumulating ozonized air to communicate momentarily with the atmosphere.

The pneumatic piston caused by the opening of valve 14, situated at the top of accumulation enclosure 16, drives out most of the ozone contained in enclosure 16, such ozone, owing to its density, tending to accumulate in the bottom of the enclosure. This valve opening re-establishes the atmospheric pressure in accumulation enclosure 16, pipe 12', processing enclosure 15, pipe 11, and main ozone destroyer 10.

A second time-lag device (not shown) closes electrically operated valves 14 and 12 after a few seconds, starting up a new cycle of accumulation of ozonized air in accumulation enclosure 16. In order to improve the effectiveness of the ozone, means (not shown) may be provided in processing enclosure 16 for stirring and/or humidifying the materials 15' to be processed and/or the gaseous environment in the processing enclosure before the next cycle of partial vacuum and injection.

The waste 15' is preferably ground up before being placed in processing enclosure 15. In a modification, this enclosure may comprise an integrated grinder. The processing enclosure may also comprise a drawer or removable inside recipient permitting the processed waste to be removed more easily and without risk.

Figure 2:
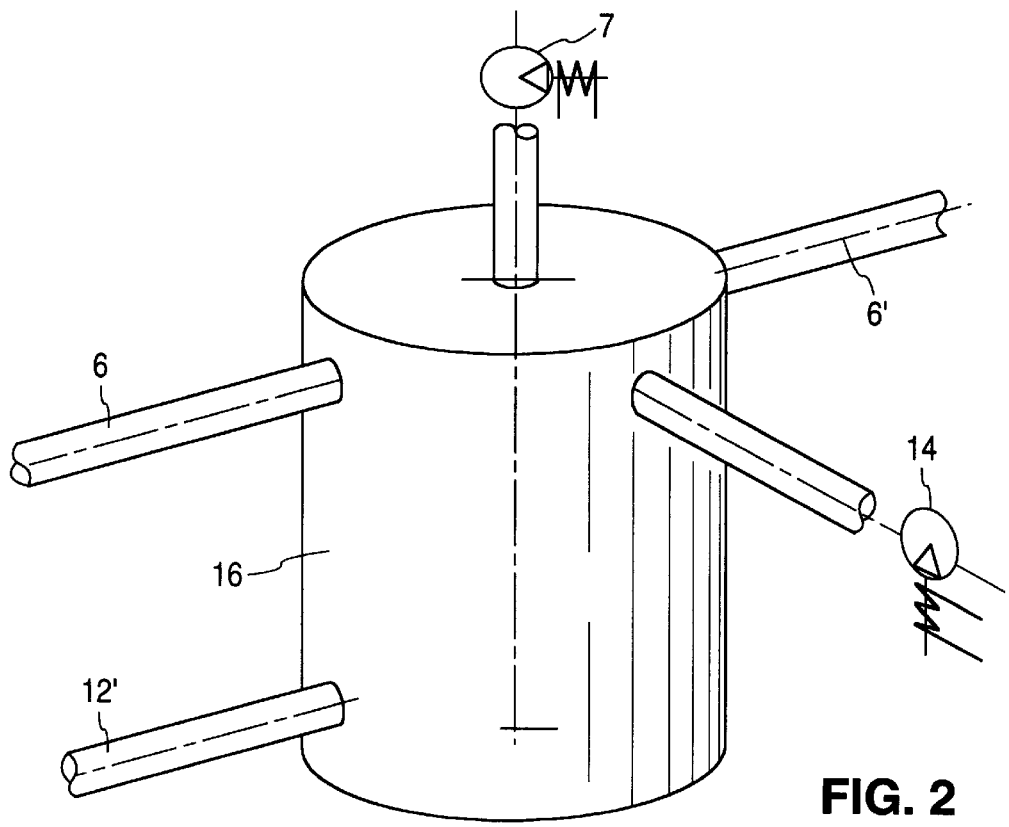
FIG. 2 is a detailed perspective view of the accumulation enclosure.

FIG. 2 shows the accumulation enclosure 16 forming part of the invention. It is composed of an airtight vertical recipient made of stainless steel or any other suitable material. The generally vertical shape and the dimensions of the enclosure are such that the ozonized air coming directly from generator 5', injected through pipe 6 into the top part of the enclosure, tends to sink by simple gravity and to accumulate at the bottom of the enclosure. A withdrawal opening connected to injection pipe 12' is provided in this bottom part of accumulation enclosure 16.

A pipe connected to electrically operated valve 14 for communication with the atmosphere likewise opens out into the top part of the accumulation enclosure. During the injection steps, the outside air reaches accumulation enclosure 16 through this pipe and through valve 14, creating a pneumatic-piston effect which aids in driving the ozone toward processing enclosure 15. The accumulation enclosure is further equipped at the top with a safety valve 7 for exhausting excess ozonized air to auxiliary ozone destroyer 8 (shown in FIG. 1).

In a modification, an assembly of pipes and valves may be provided for discharging the excess ozonized air released through safety valve 7 to main ozone destroyer 10, thus avoiding the necessity of providing an auxiliary ozone destroyer.

In another modification, means 5 for generating ozonized air are connected in closed circuit with accumulation enclosure 16 according to the principle described in the previously mentioned Australian Patent No. 4,823,393. The return coupling of the gas from enclosure 16 to the generator then also takes place in the top part of enclosure 16 through pipe 6'; in this case, safety valve 7 and auxiliary ozone destroyer 8 are unnecessary.

Figure 3:
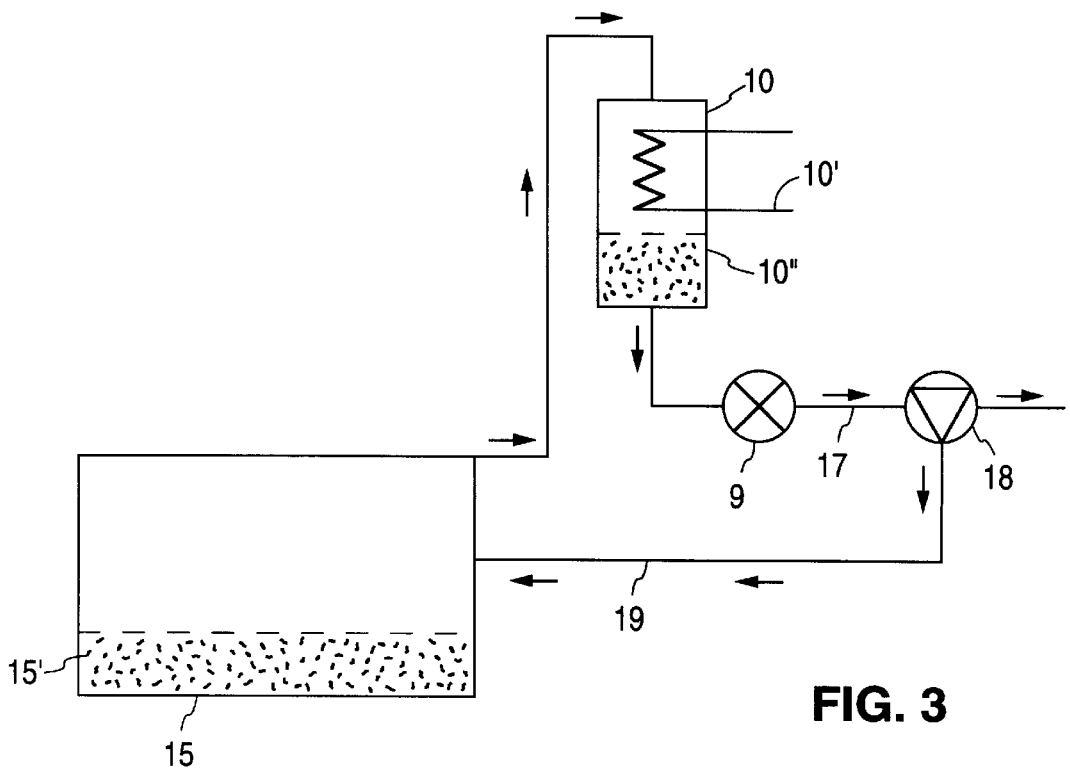
FIG. 3 is a diagram of a modification of the drain circuit in a closed-circuit connection.

FIG. 3 illustrates a modification of the drain circuit forming part of the invention, this time in a closed-circuit connection.

In sterilization applications, a drain into the atmosphere may bring about secondary recontamination of the waste due to microorganisms contained in the ambient fresh air. To remedy this drawback, in this modification a three-way valve 18 permits the air drawn off by vacuum pump 9 via ozone destroyer 10 to be reinjected during drainage into processing enclosure 15 via a reinjection pipe 19, in order to provide for the destruction of the residual ozone in a closed-loop connection. This arrangement avoids any outside contamination, the residual ozone being gradually recombined into molecular oxygen.

Although the foregoing specification relates essentially to decontamination apparatus applicable to the elimination of waste coming from a medical practice within a decontamination enclosure, the invention can be adapted without significant modification to the problem of processing, deodorizing or sterilizing hollow bodies (tubes, vats, recipients, wrappings), especially in the farm-produce, pharmaceutical, or chemical industries. Processing gases other than ozonized air may furthermore be used, depending upon the application, and additives may be used to improve the effectiveness of processing still further or to eliminate odors.

What is claimed is:

1. Apparatus for processing materials, comprising:
    a generator of processing gas;
    an enclosure for accumulating said processing gas;
    a processing enclosure into which said materials to be processed can be inserted;
    a pump that creates a partial vacuum in said processing enclosure, said vacuum pump being situated downstream from said processing enclosure and operating in air;
    a valve located upstream of the accumulating enclosure allowing the accumulating enclosure to communicate momentarily with the atmosphere; and
    a plurality of pipes interconnecting said generator, said accumulation enclosure, and said processing enclosure, said pipes being disposed in such a way that said processing gas coming from said generator can arrive in said processing enclosure after having passed through said accumulation enclosure, said materials being processed by exposure to said processing gas.

2. The apparatus of claim 1, wherein said generator of processing gas is connected in open circuit with said accumulation enclosure.

3. The apparatus of claim 1, wherein said processing gas is ozone-enriched air.

4. The apparatus of claim 3, further comprising an ozone destroyer for destroying residual ozone leaving said processing enclosure.

5. The apparatus of claim 3, further comprising a second ozone destroyer, said accumulation enclosure being provided with a safety valve opening when the pressure in said accumulation enclosure exceeds a predetermined limit in order to exhaust the accidental or momentary overpressure to said second ozone destroyer.

6. The apparatus of claim 1, further comprising an injection valve interposed between said accumulation enclosure and said processing enclosure, said injection valve being controlled by the pressure within said processing enclosure so as to trigger the injection of said processing gas into said processing enclosure.

7. The apparatus of claim 6, wherein said accumulation enclosure is a fluid-tight recipient comprising an opening in the bottom part thereof, said processing gas coming from said generator being introduced into the top part of said recipient and exhausted to said processing enclosure through said opening.

8. The apparatus of claim 6, wherein said valve enabling communication with the atmosphere places the whole apparatus under atmospheric pressure and drives most of said processing gas contained in said accumulation enclosure toward said processing enclosure.

9. Apparatus for processing materials, comprising:
    a generator of ozone-enriched air;
    an enclosure for accumulating said ozone-enriched air,
    a processing enclosure into which said materials to be processed can be inserted;
    a pump that creates a vacuum in said processing enclosure, said vacuum pump being situated downstream from said processing enclosure and operating in air;
    a valve located upstream of the accumulating enclosure allowing the accumulating enclosure to communicate momentarily with the atmosphere; and a plurality of pipes interconnecting said generator, said accumulation enclosure, and said processing enclosure, said pipes being disposed in such a way that said ozone-enriched air coming from said generator can arrive in said processing enclosure after having passed through said accumulation enclosure, said generator being connected in open rust with said accumulation closure, said materials being processed by exposure to said ozone-enriched air.

10. The apparatus of claim 9, further comprising an ozone destroyer for destroying residual ozone leaving said processing enclosure.

11. The apparatus of claim 9, further comprising a second ozone destroyer, said accumulation enclosure being provided with a safety valve opening when the pressure in said accumulation enclosure exceeds a predetermined limit in order to exhaust the overpressure to said second ozone destroyer.

12. The apparatus of claim 9, further comprising an injection valve interposed between said accumulation enclosure and said processing enclosure, said injection valve being controlled by the pressure within said processing enclosure so as to trigger the injection of said ozone-enriched air into said processing enclosure.

13. The apparatus of claim 9, wherein said accumulation enclosure is a fluid-tight recipient comprising an opening in the bottom part thereof, said ozone-enriched air coming from said generator being introduced into the top part of said recipient and exhausted to said processing enclosure through said opening.

14. The apparatus of claim 9, wherein said valve enabling communication with the atmosphere places the whole apparatus under atmospheric pressure and drives most of said ozone-enriched air contained in said accumulation enclosure toward said processing enclosure.

15. Apparatus for processing materials, comprising:
   a generator of ozone-enriched air;
   an fluid-tight recipient for accumulating said ozone-enriched air, said fluid-tight recipient comprising an opening in the bottom part thereof and being equipped with a valve enabling communication with the atmosphere for placing the whole apparatus under atmospheric pressure;
   a processing enclosure into which said materials to be processed can be inserted;
   a valve allowing the fluid-tight recipient enclosure to communicate momentarily with the atmosphere to drive the ozone-enriched air contained in said accumulation enclosure toward said processing enclosure;
   a first ozone destroyer for destroying residual ozone leaving said processing enclosure;
   a vacuum pump situated downstream from said first ozone destroyer and that creates a vacuum in said processing enclosure, said vacuum pump operating in air;
   a plurality of pipes interconnecting said generator, said fluid-tight recipient, and said processing enclosure, said pipes being disposed in such a way that said ozone-enriched air coming from said generator can arrive in said processing enclosure after having being introduced into the top part of said fluid-tight recipient and being exhausted to said processing enclosure through said opening in the bottom part of said fluid-tight recipient, said generator of ozone-enriched air being connected in open circuit with said fluid-tight recipient;
   a second ozone destroyer, said fluid-tight recipient being provided with a safety valve opening when the pressure in said fluid-tight recipient exceeds a predetermined limit in order to exhaust the overpressure to said second ozone destroyer; and
   an injection valve interposed between said fluid-tight recipient and said processing enclosure, said injection valve being controlled by the pressure within said processing enclosure so as to trigger the sudden and forceful injection of said ozone-enriched air into said processing enclosure.

16. A method of processing materials, comprising a plurality of separate steps of:
   accumulating a processing gas in an accumulation enclosure;
   creating a partial vacuum in a processing enclosure;
   injecting the processing gas into the processing enclosure, based on the pressure in the processing enclosure; and
   opening a valve coupled to an upper portion of the accumulation enclosure to drive out the processing gas contained in the accumulation enclosure and to reestablish atmospheric pressure in the accumulation enclosure.

17. The method of claim 16, wherein the processing gas is ozone-enriched air.

18. The method of claim 17, wherein the step of creating a partial vacuum in the processing enclosure further comprises the respective steps of creating a partial vacuum in the processing enclosure prior to each of the separate steps of injection of ozone-enriched processing air into the processing enclosure.

19. The method of claim 18, further comprising the respective steps of stirring the contents of the processing enclosure between each of the steps of injection and of creating a partial vacuum.

20. The method of claim 17, wherein the injection of ozone-enriched air is carried out by restoring the apparatus to atmospheric pressure.

21. A method of processing materials, comprising a plurality of separate steps of:
   creating a vacuum in a processing enclosure;
   accumulating a processing gas in an accumulation enclosure;
   injecting ozone-enriched air into said processing enclosure, based on the pressure of the accumulation enclosure;
   opening a valve coupled to an upper portion of the accumulation enclosure to drive out the processing gas contained in the accumulation enclosure and to reestablish atmospheric pressure in the accumulation enclosure; and
   stirring the contents of said processing enclosure.

22. The method of claim 21, wherein the injection of ozone-enriched air is carried out by restoring the apparatus to atmospheric pressure.

* * * * *